(12) United States Patent
Shimuta (10) Patent No.: US 12,201,407 B2
(45) Date of Patent: Jan. 21, 2025

(54) GRIP-TYPE PULSE WAVE MEASURING DEVICE

(71) Applicant: Murata Manufacturing Co., Ltd., Nagaokakyo (JP)

(72) Inventor: Toru Shimuta, Nagaokakyo (JP)

(73) Assignee: MURATA MANUFACTURING CO., LTD., Nagaokakyo (JP)

( * ) Notice: Subject to any disclaimer, the term of this patent is extended or adjusted under 35 U.S.C. 154(b) by 1228 days.

(21) Appl. No.: 16/351,739

(22) Filed: Mar. 13, 2019

(65) Prior Publication Data

US 2019/0209029 A1 Jul. 11, 2019

Related U.S. Application Data

(63) Continuation of application No. PCT/JP2017/033457, filed on Sep. 15, 2017.

(30) Foreign Application Priority Data

Oct. 7, 2016 (JP) ................................ 2016-199557

(51) Int. Cl.
*A61B 5/021* (2006.01)
*A61B 5/024* (2006.01)
*A61B 5/00* (2006.01)

(52) U.S. Cl.
CPC ...... *A61B 5/02108* (2013.01); *A61B 5/02141* (2013.01); *A61B 5/02416* (2013.01); *A61B 5/6826* (2013.01); *A61B 2560/0425* (2013.01)

(58) Field of Classification Search
CPC ............ A61B 5/02108; A61B 5/02141; A61B 5/02416; A61B 5/6826; A61B 2560/0425
See application file for complete search history.

(56) References Cited

U.S. PATENT DOCUMENTS 4,332,258 A * 6/1982 Arai .................... A61B 5/02433
600/479
10,624,549 B2 * 4/2020 Shimuta ................. A61B 5/316
(Continued)

FOREIGN PATENT DOCUMENTS

JP H1043150 A 2/1998
JP 2007289463 A 11/2007
(Continued)

OTHER PUBLICATIONS

International Search Report issued in PCT/JP2017/033457, date of mailing Oct. 31, 2017.
(Continued)

*Primary Examiner* — Navin Natnithithadha
(74) *Attorney, Agent, or Firm* — ArentFox Schiff LLP (57) ABSTRACT

A grip-type pulse wave measuring device includes a main body that has a substantially spheroid shape, and a stopper that projects along an axial direction of the main body and abuts against a side surface of a thumb to restrict a position of the thumb when a user grips the main body portion. Moreover, a light shielding cover is provided that is formed into a substantially semi-cylindrical shape and is mounted so as to be swingable about, as a swing shaft, a shaft that is provided in parallel to the axial direction of the main body. A photoplethysmographic sensor is disposed at a position offset from the swing shaft of the light shielding cover along a peripheral direction of the main body and is configured to acquire a photoplethysmographic signal.

18 Claims, 7 Drawing Sheets

(56) References Cited

U.S. PATENT DOCUMENTS

| | | | |
|---|---|---|---|
| 11,432,730 B2* | 9/2022 | Shimuta | A61B 5/02427 |
| 2003/0036685 A1* | 2/2003 | Goodman | G16H 70/20 |
| | | | 600/300 |
| 2003/0097078 A1* | 5/2003 | Maeda | A61B 5/339 |
| | | | 600/509 |
| 2005/0004487 A1* | 1/2005 | Ishida | A61B 5/7445 |
| | | | 600/523 |
| 2009/0015558 A1* | 1/2009 | Hung | A61B 5/02416 |
| | | | 345/163 |
| 2009/0096748 A1* | 4/2009 | Wu | A61B 5/02055 |
| | | | 345/157 |
| 2013/0261414 A1* | 10/2013 | Tal | A61B 5/332 |
| | | | 600/324 |
| 2013/0281868 A1* | 10/2013 | Kawachi | A61B 5/14552 |
| | | | 600/485 |
| 2013/0310659 A1* | 11/2013 | Kawachi | A61B 5/02125 |
| | | | 600/301 |
| 2014/0088396 A1* | 3/2014 | Shimuta | A61B 5/02427 |
| | | | 600/382 |
| 2015/0141774 A1 | 5/2015 | Ogawa et al. | |
| 2015/0201876 A1* | 7/2015 | Zhou | A61B 5/14552 |
| | | | 600/323 |
| 2018/0064355 A1* | 3/2018 | Shimuta | A61B 5/316 |
| 2019/0209029 A1* | 7/2019 | Shimuta | A61B 5/02108 |
| 2019/0231205 A1* | 8/2019 | Shimuta | A61B 5/332 |
| 2020/0000352 A1* | 1/2020 | Shimuta | A61B 5/02427 |
| 2020/0138369 A1* | 5/2020 | Shimuta | G16H 40/63 |
| 2022/0280107 A1* | 9/2022 | Shimuta | A61B 5/00 |

FOREIGN PATENT DOCUMENTS

| | | |
|---|---|---|
| JP | 2009005842 A | 1/2009 |
| JP | 2009066042 A | 4/2009 |
| JP | 2014068836 A | 4/2014 |

OTHER PUBLICATIONS

Written Opinion of the International Searching Authority issued in PCT/JP2017/033457, date of mailing Oct. 31, 2017.

* cited by examiner

GRIP-TYPE PULSE WAVE MEASURING DEVICE

CROSS-REFERENCE TO RELATED APPLICATIONS

The present application is a continuation of PCT/JP2017/033457 filed Sep. 15, 2017, which claims priority to Japanese Patent Application No. 2016-199557, filed Oct. 7, 2016, the entire contents of each of which are incorporated herein by reference.

TECHNICAL FIELD

The present disclosure relates to a grip-type pulse wave measuring device that acquires a pulse wave signal.

BACKGROUND

In recent years, there has been increasing people's interest in management, maintenance, and enhancement of health. It has been therefore desired that people can more easily obtain biological information such as pulse and electrocardiogram in everyday life. Patent Document 1 (identified below) discloses a pulse wave measuring device that measures pulse waves by causing a user to grip a main body portion and insert his/her index finger into a finger insertion portion. In addition, Patent Document 2 (also identified below) discloses a pulse wave detecting device that can be gripped by the hand for use.

More specifically, the pulse wave measuring device disclosed in Patent Document 1 includes the finger insertion portion into which a finger tip of a subject can be inserted and that has a light emitting element and a light receiving element arranged so as to face an inner portion of the fingertip. Moreover, the main body portion supports the finger insertion portion in a rotationally movable manner using, as a fulcrum, with a portion on the front side in the insertion direction of the finger tip. The subject who performs pulse wave measurement can measure the pulse waves by inserting the index finger through an insertion port of the finger insertion portion while gripping the main body portion by the right hand or the left hand.

In the pulse wave detecting device disclosed in Patent Document 2, a pulse wave detector into which a finger tip of a finger is inserted is provided near a center of a main body portion, and a movable portion is movably mounted on the pulse wave detector. The movable portion is biased toward the pulse wave detector side by a spring. This device also measures pulse waves by causing a user to insert his/her finger into the pulse wave detector.

Patent Document 1: Japanese Unexamined Patent Application Publication No. 2009-66042.
Patent Document 2: Japanese Unexamined Patent Application Publication No. 10-43150.

In the pulse wave measuring device disclosed in Patent Document 1, it is necessary to fix the main body portion such that the main body portion does not move when the subject inserts his/her finger. Therefore, in this pulse wave measuring device, non-slip rubber is stuck on a bottom surface such that the main body portion does not slip and move. Accordingly, this pulse wave measuring device can be used only on, for example, a desk or the like, and there is a problem that the place of use is limited.

On the other hand, with the pulse wave measuring device disclosed in Patent Document 2, although limitation of the place of use is eliminated, it is necessary to insert the index finger into the pulse wave detector provided near the center of the main body portion while gripping the device by four fingers except the index finger, and thus an unnatural movement is forced. Moreover, it is difficult to stably measure the pulse waves for a long time because of such an unnatural holding manner.

SUMMARY OF THE INVENTION

The exemplary embodiments of the invention has been made in order to solve the above-described problems. Accordingly, it is an object thereof to provide a grip-type pulse wave measuring device that is configured to stably acquire pulse waves only by naturally being gripped by one hand without any limit of a place of use.

In an exemplary aspect, a grip-type pulse wave measuring device includes a main body that has a substantially spheroid shape, a stopper that projects along an axial direction of the main body and abuts against a side surface of a thumb to restrict a position of the thumb when a user grips the main body by one hand. Moreover, a pulse wave sensor is disposed at a position offset from the stopper portion along a peripheral direction of the main body portion and is configured to acquire a pulse wave signal from a finger tip of the thumb restricted by the stopper portion. Yet further, a step portion is formed on the main body portion at a position closer to a tip portion at a back surface side when seen from the stopper side. The step portion is formed such that when the user grips the main body portion while making an index finger be along the step portion, the finger tip of the thumb is guided to a position of the pulse wave sensor.

With the grip-type pulse wave measuring device according to the exemplary aspect, the stopper projects along the axial direction of the main body such that it abuts against the side surface of the thumb to restrict the position of the thumb when the user grips the main body portion by one hand. Further, the step portion is formed on the main body at the position closer to the tip portion at the back surface side when seen from the stopper side. More specifically, the step portion is formed such that when the user grips the main body while making the index finger be along the step portion, the thumb is guided to the position of the pulse wave sensor. Thus, when the user grips the device (main body portion) by one hand, the thumb and the index finger can be guided to appropriate gripping positions by the stopper and the step portion. Therefore, when the user grips the device (i.e., the main body), the positions of the respective fingers are fixed substantially constant, and variations in the position of the finger tip of the thumb (i.e., variations in the position thereof relative to the pulse wave sensor) can be suppressed. As a result, the pulse waves can be stably acquired only by naturally gripping the device by one hand without any limit of the place of use. In addition, since the step portion catches the index finger, the user is not required to firmly grip the main body portion and hardly feels fatigue even if he/she grips the device (main body portion) for a relatively long time.

Further, in the grip-type pulse wave measuring device according to the exemplary aspect, it is preferable that an area of the main body in which the pulse wave sensor is disposed be recessed inward from a peripheral surface.

With this configuration, the user can reliably locate the finger tip of the thumb on the pulse wave sensor without looking at the device by positioning an inner portion of the finger tip of the thumb on the recess. In particular, even when it is difficult to visually check the pulse wave sensor (photoplethysmographic sensor) due to a light shielding cover, a position (a position of the pulse wave sensor) where the finger tip of the thumb is placed can be recognized by sense of touch. Therefore, positional variations in the finger tip of the thumb in the lateral direction and the vertical direction can be prevented or minimized, and stable pulse wave measurement can be performed. Further, when the thumb is held for a long time in a stretched state of a first joint, the user feels fatigue in the thumb. The pulse wave sensor is however located in the area recessed inward from the peripheral surface, so that the thumb is bent moderately and the user fatigue in the thumb can also be eliminated or minimized.

It is preferable that the grip-type pulse wave measuring device according to the exemplary aspect further includes a light shielding cover which is formed into a substantially semi-cylindrical shape and is disposed so as to cover an upper portion of the pulse wave sensor. In this aspect, the pulse wave sensor is a photoplethysmographic sensor which has a light emitting element and a light receiving element and acquires a photoplethysmographic signal.

In this case, since the light shielding cover covers the photoplethysmographic sensor to prevent disturbance light from entering the sensor, it is possible to stably acquire (measure) the photoplethysmographic signal.

In the grip-type pulse wave measuring device according to the exemplary aspect, it is preferable that the light shielding cover be mounted so as to be swingable in the peripheral direction of the main body portion.

With this configuration, when, in measurement, the user grips the device (main body portion) by one hand, moves his/her thumb as a measurement site onto the pulse wave sensor, and causes the light shielding cover to swing and be closed, the light shielding cover covers the thumb to prevent the disturbance light from entering the sensor, so that the stable measurement can be performed.

In the grip-type pulse wave measuring device according to the exemplary aspect, it is preferable that the light shielding cover include a biasing member which biases the light shielding cover in a direction in which the light shielding cover is opened, and be mounted so as to be swingable such that when seen from a base end portion side of the main body, one end portion protrudes toward the pulse wave sensor side relative to the stopper portion in an open state, and the one end portion substantially is flush with the stopper portion in a closed state.

With this configuration, when the user grips the device (i.e., the main body) by one hand and moves his/her thumb as the measurement site onto the pulse wave sensor, the light shielding cover can be made to swing and be closed by being pushed by the thumb. On the other hand, the light shielding cover can be made to be automatically opened when the device (main body) is not gripped. Therefore, the light shielding cover does not become obstructive in gripping of the device. Thus, the user can naturally grip the device (main body) without being forced to perform an unnatural movement when gripping the device (main body).

In the grip-type pulse wave measuring device according to the exemplary aspect, it is preferable that the light shielding cover be mounted so as to be swingable about, as a swing shaft, a shaft provided substantially in parallel to the axial direction of the main body portion.

With this configuration, with a series of natural movements of gripping the device (i.e., the main body) and causing the thumb to slide laterally and move onto the pulse wave sensor, the light shielding cover can be made to swing and be closed so as to cover the finger tip of the thumb.

It is preferable that the grip-type pulse wave measuring device according to the exemplary aspect further includes a lock mechanism which locks the light shielding cover in a closed state.

With this configuration, the light shielding cover can be fixed in the closed state while the device is not used, so that it is possible to reduce the possibility of breakage, for example, even when it is carried, dropped, and so on.

According to the exemplary aspects of the present invention, it is possible to stably acquire pulse waves only by naturally gripping the device by one hand without any limit of the place of use.

DETAILED DESCRIPTION OF EMBODIMENTS

Hereinafter, exemplary embodiments will be described in detail with reference to the accompanying drawings. It is noted that in the drawings, the same or corresponding parts are denoted by the same reference numerals. In addition, in each of the drawings, the same elements are denoted by the same reference numerals, and overlapped description thereof will be omitted.

Figure 1:
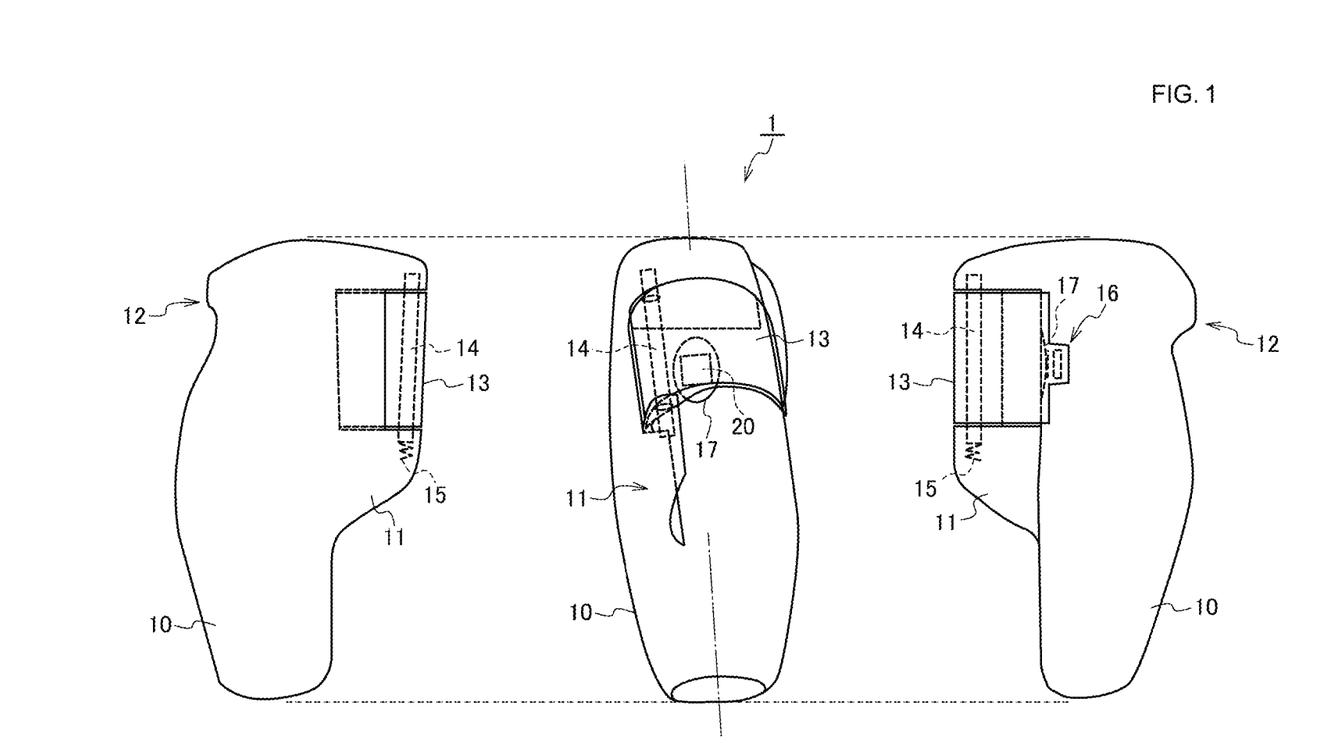
FIG. 1 illustrates a front view and right and left side views for an appearance (a state in which a light shielding cover is closed) of a grip-type pulse wave measuring device according to an exemplary embodiment.
Figure 2:
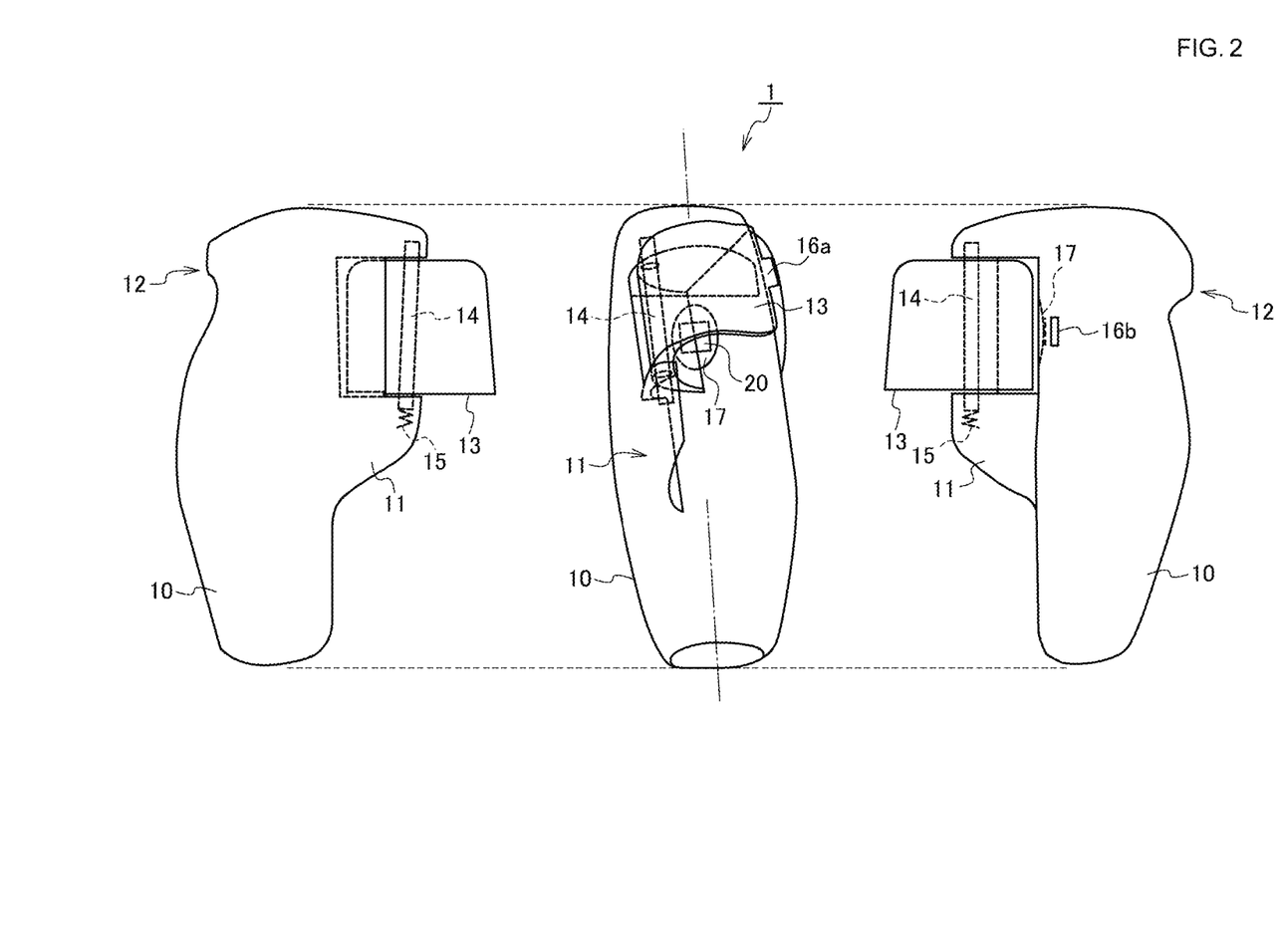
FIG. 2 illustrates a front view and right and left side views for an appearance (a state in which the light shielding cover is opened) of the grip-type pulse wave measuring device according to the exemplary embodiment.
Figure 3:
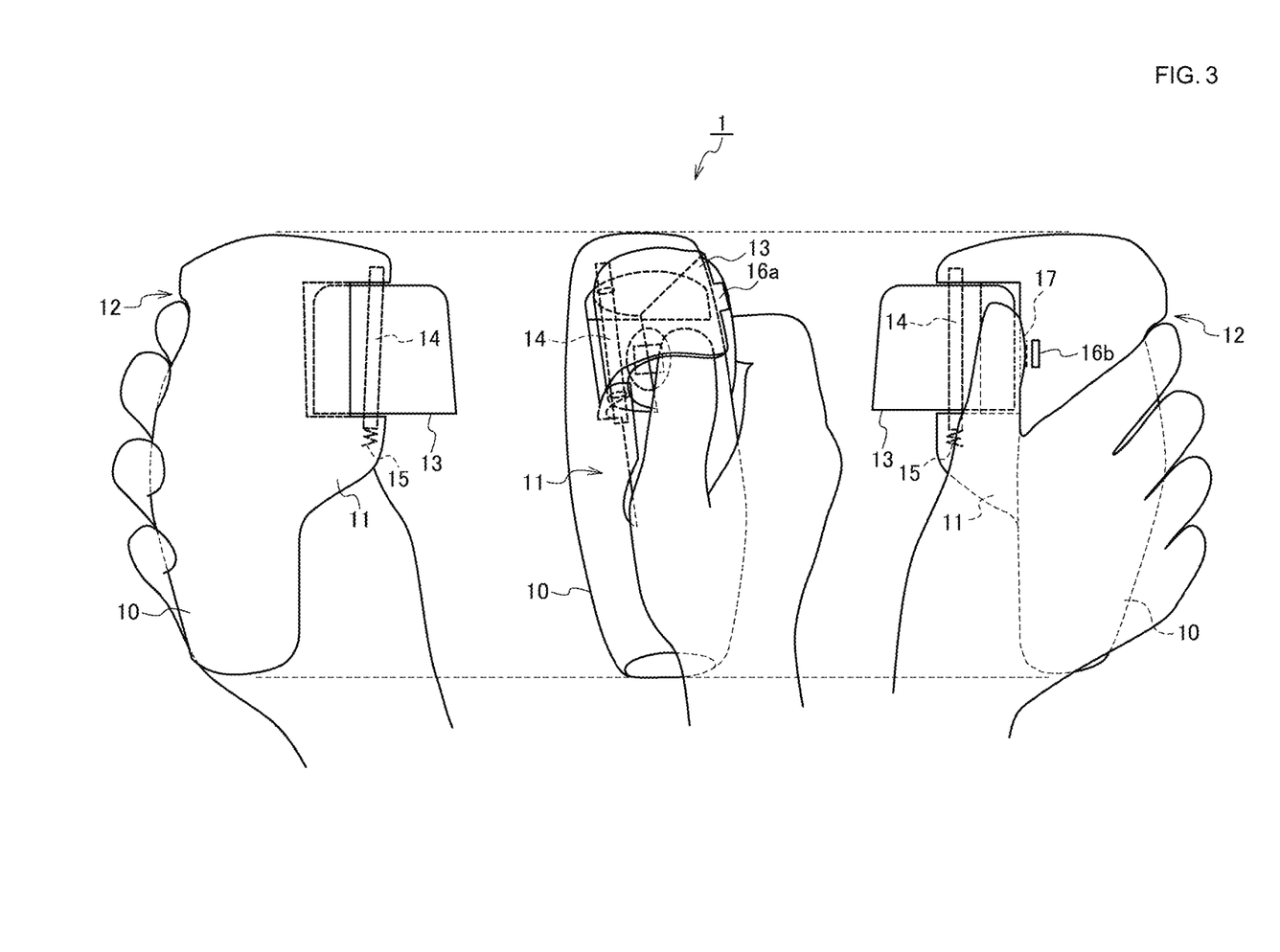
FIG. 3 is a view illustrating a state (a state before measurement) in which the grip-type pulse wave measuring device according to the exemplary embodiment is gripped by the hand.
Figure 4:
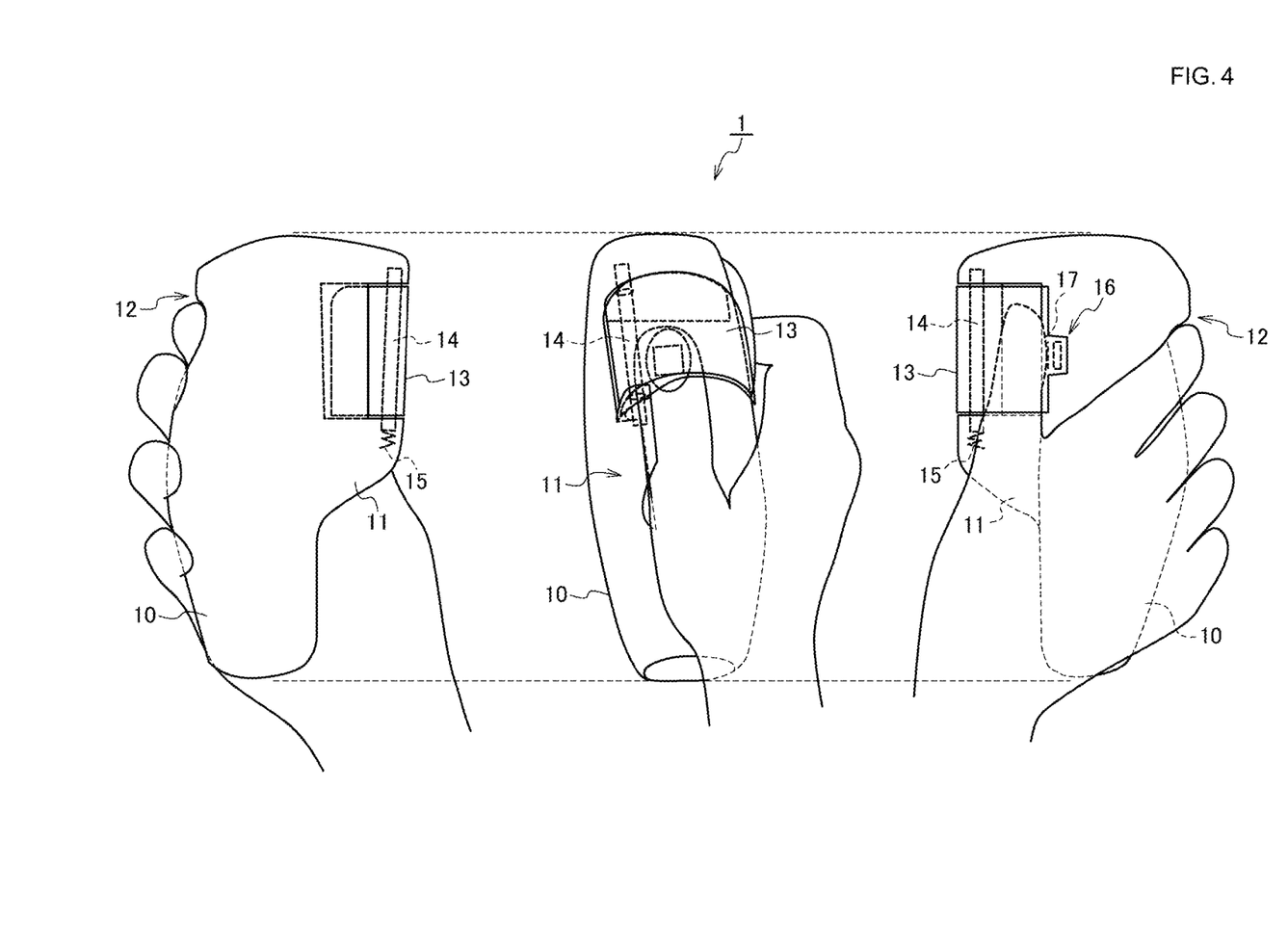
FIG. 4 is a view illustrating a state (a state in measurement) in which the grip-type pulse wave measuring device according to the exemplary embodiment is gripped by the hand.
Figure 5:
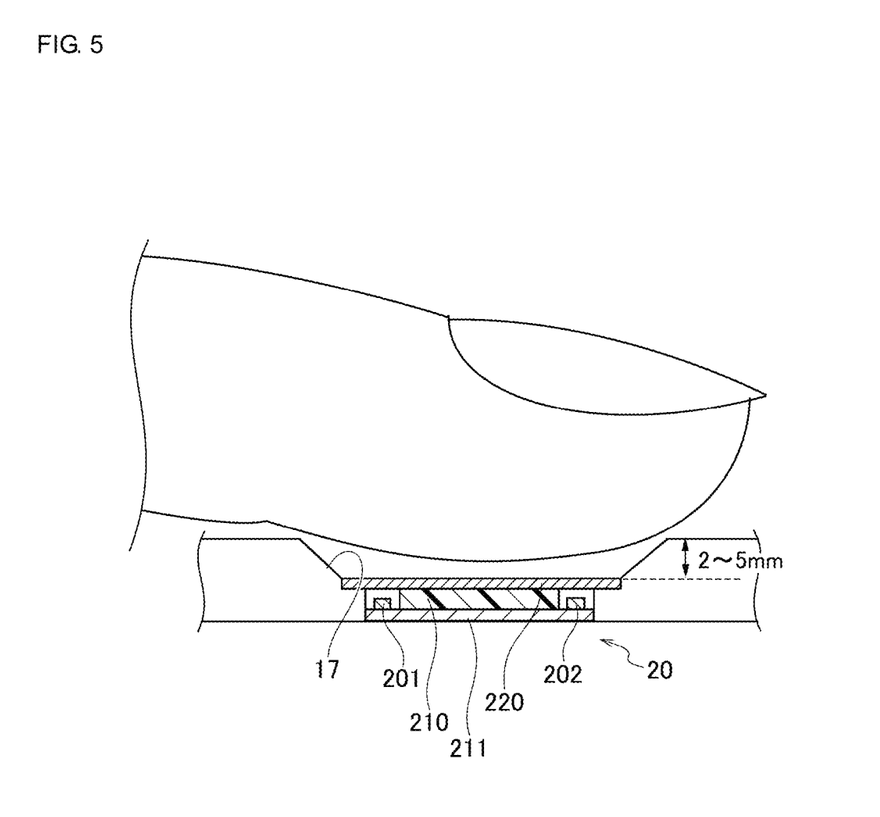
FIG. 5 is an enlarged cross-sectional view of a recess (concave portion) formed in a surface of a main body portion of the grip-type pulse wave measuring device according to the exemplary embodiment.
Figure 6:
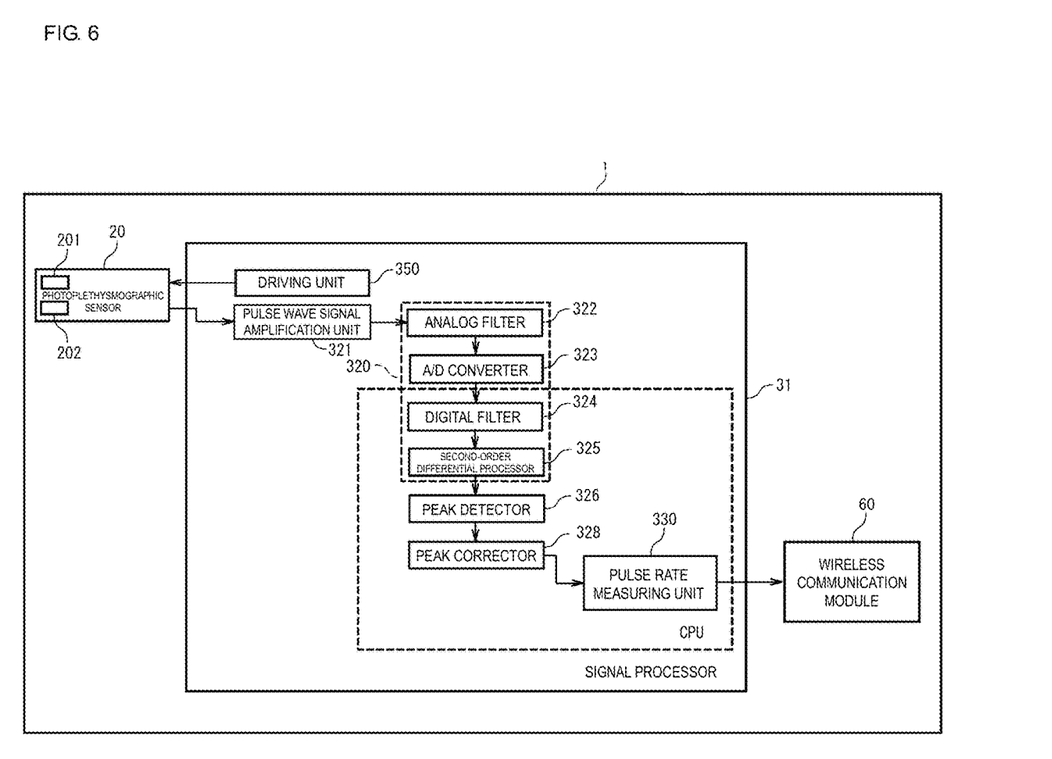
FIG. 6 is a block diagram illustrating the functional configuration of the grip-type pulse wave measuring device according to the exemplary embodiment.

First, the configuration of a grip-type pulse wave measuring device 1 according to the exemplary embodiment will be described with reference to FIG. 1 to FIG. 6. FIG. 1 illustrates a front view and right and left side views for an appearance (a state in which a light shielding cover is closed) of the grip-type pulse wave measuring device 1 according to the embodiment, and FIG. 2 illustrates a front view and right and left side views for an appearance (a state in which the light shielding cover is opened) of the grip-type pulse wave measuring device 1. FIG. 3 is a view illustrating a state (a state before measurement) in which the grip-type pulse wave measuring device 1 is gripped by the hand, and FIG. 4 is a view illustrating a state (a state in measurement) in which the grip-type pulse wave measuring device 1 is gripped by the hand. FIG. 5 is an enlarged cross-sectional view of a recess (concave portion) 17 formed in a surface of a main body portion 10 of the grip-type pulse wave measuring device 1. FIG. 6 is a block diagram illustrating the functional configuration of the grip-type pulse wave measuring device 1.

The grip-type pulse wave measuring device 1 is a pulse wave measuring device of a grip type that is configured to acquire photoplethysmographic waves from a finger tip of a thumb and measuring a pulse rate and the like by being gripped by one hand of a user.

The grip-type pulse wave measuring device 1 has a main body portion 10 (i.e., a main body) that has a contoured shape configured to be gripped by a hand of a user. In an exemplary aspect, the main body portion 10 is formed into a substantially spheroid shape that the user grips by the thumb and the other four fingers of the right hand (or the left hand) in measurement. In the main body portion 10, a stopper portion (locking portion or simply a stopper) 11, which abuts against a side surface of a middle joint and/or a base joint of the thumb to restrict (stop) a position of the thumb when the user grips the main body portion 10 by one hand, projects along the axial direction (see a dashed-dotted line in FIGS. 1 and 2) of the main body portion 10. It is preferable that the main body portion 10 be made of, for example, resin or the like. Also, it should be appreciated that the term "substantially spheroid shape" is intended not to be limited to the spheroid in a strict sense defined by geometry.

A step portion 12 (i.e., a protrusion or protruding member or step or finger guiding member) for guiding an index finger to an appropriate gripping position when the user grips the main body portion 10 (device 1) is formed in the main body portion 10 at a position closer to a tip portion (i.e., an end of the main body) than the center at the back surface side when seen from the stopper portion 11 side. In other words, when the user grips the main body portion 10 (device 1) while positioning the index finger along the step portion 12, the positions of the respective fingers are fixed substantially constant, and variations in the position of the finger tip of the thumb in the vertical direction (i.e., variations in the position thereof relative to a photoplethysmographic sensor 20, which will be described later) can be suppressed by the step portion 12 positioning the hand of the user to physically guide the finger tip of the thumb to the photoplethysmographic sensor 20.

Further, a light shielding cover (light shielding member) 13 having a light shielding function and shielding light so as to prevent disturbance light from entering the photoplethysmographic sensor 20, which will be described later, in measurement is mounted on the main body portion 10 in an openable/closable manner by swinging in the peripheral direction of the main body portion 10. The light shielding cover 13 is formed into a substantially semi-cylindrical shape (curved planar shape) so as to cover a user's thumb in measurement.

More specifically, the light shielding cover 13 is mounted on the main body portion 10 at the tip side of the stopper portion 11 (the main body portion 10) along the stopper portion 11 of the main body portion 10 so as to be swingable about, as a swing shaft 14, a shaft provided substantially in parallel to the axial direction of the main body portion 10. More specifically, the light shielding cover 13 is mounted so as to be swingable such that when seen from a base end portion side of the main body portion 10, one end portion (end side) thereof protrudes toward the photoplethysmographic sensor 20 side relative to the stopper portion 11 in an open state, and the one end portion (end side) thereof substantially is flush with the end surface of the stopper portion 11 in a closed state.

Further, a biasing member 15, such as a spring, for example, is provided and configured to bias the light shielding cover 13 in the direction of opening it is incorporated in the swing shaft 14 of the light shielding cover 13. Therefore, the light shielding cover 13 is opened automatically when the lock is released (details of which will be described later) and the user does not grip the main body portion 10. In this aspect, the light shielding cover 13 swings and is closed so as to cover the finger tip of the thumb with a movement of moving the thumb till the thumb abuts against the stopper portion 11 when the user grips the main body portion 10.

Further, the light shielding cover 13 has a lock mechanism 16 configured to lock (i.e., fix) the light shielding cover 13 in the closed state, for example, when not in use. More specifically, in an exemplary aspect, a claw portion 16a is formed on one end portion (end side) of the light shielding cover 13 and a groove portion 16b into which the claw portion 16a is fitted is formed in the side surface of the main body portion 10. The claw portion 16a formed on the end portion of the light shielding cover 13 is fitted into the groove portion 16b, so that the light shielding cover 13 is fixed (locked) to the main body portion 10.

The photoplethysmographic sensor 20 is disposed on the main body portion 10 at a position (a position on the center line of the main body portion 10) which is offset from the swing shaft 14 of the light shielding cover 13 along the peripheral direction of the main body portion 10. The photoplethysmographic sensor 20 has a light emitting element 201 and a light receiving element 202, and acquires a photoplethysmographic signal from the finger tip of the thumb restricted by the stopper portion 11. The photoplethysmographic sensor 20 is a sensor which optically detects the photoplethysmographic signal by utilizing light absorption characteristics of hemoglobin in blood.

As further shown in FIG. 5, for example, in the main body portion 10, an area in which the photoplethysmographic sensor 20 having the light emitting element 201 and the light receiving element 202 is disposed is recessed inward in an approximately elliptical shape from the peripheral surface. In other words, the photoplethysmographic sensor 20 is disposed at the center of the recess 17 formed in the main body portion 10. The user can therefore reliably locate the finger tip of the thumb on the photoplethysmographic sensor 20 without needing to see the sensor 20 by simply putting an inner portion of the thumb on the recess (concave portion) 17 and positioning the finger tip of the thumb by a tactile sensation. More particularly, as illustrated in FIG. 5, the recess 17 is preferably recessed from the surface of the main body portion 10 by about 2 to 5 mm.

In FIG. 5, a reference numeral 210 denotes a light shielding portion, and a reference numeral 220 denotes a transparent cover. The light shielding portion 210 is formed by filling a region between the light emitting element 201 and the light receiving element 202 on the main surface of a wiring board 211 with resin having a light shielding property. For example, epoxy resin containing light shielding powder such as carbon black, or the like is suitably used for the light shielding portion 210. Further, the transparent cover 220 is formed of, for example, acrylic, polycarbonate, PET (polyethylene terephthalate), or the like, which has a light-transmitting property.

As illustrated in FIG. 6, the light emitting element 201 emits light in response to a pulse driving signal output from a driving unit 350 of a signal processor 31 to be described later. As the light emitting element 201, for example, an LED, a VCSEL (Vertical Cavity Surface Emitting Laser), a resonator-type LED, or the like can be used. It is noted that the driving unit 350 is configured to generate and output the pulse driving signal that drives the light emitting element 201.

Moreover, the light receiving element 202 is configured to output a detection signal corresponding to the intensity of light that is emitted from the light emitting element 201, passes through the thumb or is reflected by the thumb, and is incident thereon. As the light receiving element 202, for example, a photodiode, a phototransistor, or the like is suitably used. In this embodiment, the photodiode is used as the light receiving element 202.

The light receiving element 202 is connected to the signal processor 31, and the detection signal (photoplethysmographic signal) obtained by the light receiving element 202 is output to the signal processor 31. The signal processor 31 processes the input photoplethysmographic signal and measures a pulse rate, a pulse interval, and the like.

In this case, the main body portion 10 accommodates therein the signal processor 31 and a wireless communication module 60 that transmits biological information such as the measured photoplethysmographic signal and pulse rate to an external device. In addition, the main body portion 10 accommodates therein a battery (not illustrated) that supplies electric power to the photoplethysmographic sensor 20, the signal processor 31, the wireless communication module 60, and the like.

According to the exemplary aspect, the signal processor 31 includes an amplification unit 321, a signal processor 320, a peak detector 326, a peak corrector 328, and a pulse rate measuring unit 330. Further, the signal processor 320 includes an analog filter 322, an A/D converter 323, a digital filter 324, and a second-order differential processor 325.

In the above-described units, the digital filter 324, the second-order differential processor 325, the peak detector 326, the peak corrector 328, and the pulse rate measuring unit 330 are configured by a CPU for performing arithmetic processing, a ROM for storing a program and data for causing the CPU to execute pieces of processing, a RAM for temporarily storing various pieces of data such as an arithmetic result, and the like. In other words, the CPU executes the program stored in the ROM to implement the functions of the units described above.

The amplification unit 321 is configured by, for example, an amplifier using an operational amplifier or the like and amplifies the photoplethysmographic signal detected by the photoplethysmographic sensor 20. The photoplethysmographic signal amplified by the amplification unit 321 is output to the signal processor 320.

As described above, the signal processor 320 includes the analog filter 322, the A/D converter 323, the digital filter 324, and the second-order differential processor 325, and extracts a pulse component by performing filtering processing and second-order differential processing on the photoplethysmographic signal amplified by the amplification unit 321.

The analog filter 322 and the digital filter 324 perform filtering for removing components (noise) other than frequencies characterizing the photoplethysmographic signal and improving S/N. More specifically, since frequency components of 0.1 to around several tens of Hz are dominant for the photoplethysmographic signal. Therefore, the digital filter 324 and the analog filter 322 such as a low pass filter and a band pass filter are used to perform the filtering processing thereon and selectively transmit only signals in the above-described frequency range, so that the S/N is improved.

In addition, when only extraction of the pulsation component is intended (i.e., when it is not necessary to obtain a waveform and the like), a passing frequency range may be further narrowed to block off components other than the pulsation component in order to improve noise resistance. In addition, both of the analog filter 322 and the digital filter 324 need not be necessarily provided, and only one of the analog filter 322 and the digital filter 324 may be provided. The photoplethysmographic signal that has been subjected to the filtering process by the analog filter 322 and the digital filter 324 is output to the second-order differential processor 325.

The second-order differential processor 325 acquires second-order differential pulse waves (acceleration pulse waves) by performing second-order differentiation on the photoplethysmographic signal. The acquired acceleration pulse waves are output to the peak detector 326. Since rising points of the photoplethysmographic waves are not clear and are not easily detected in some cases, it is preferable that the peak detection be performed after converting the photoplethysmographic waves into the acceleration pulse waves. It is however not essential to provide the second-order differential processor 325 and the second-order differential processor 325 may be omitted.

Moreover, the peak detector 326 is configured to detect peaks of the photoplethysmographic signal (acceleration pulse waves) that has been subjected to the filtering processing by the signal processor 320. It is noted that the peak detector 326 performs the peak detection within a normal range of the pulse interval and stores pieces of information such as the peak time and the peak amplitude in the RAM or the like for each of all the detected peaks.

The peak corrector 328 obtains a delay time of the photoplethysmographic signal in the signal processor 320 (the analog filter 322, the digital filter 324, and the second-order differential processor 325). The peak corrector 328 corrects the peaks of the photoplethysmographic signal (acceleration pulse waves), which have been detected by the peak detector 326, based on the obtained delay time of the photoplethysmographic signal. The corrected peaks of the photoplethysmographic signal (acceleration pulse waves) are output to the pulse rate measuring unit 330.

The pulse rate measuring unit 330 obtains the pulse rate from the interval between the peaks of the photoplethysmographic signal (acceleration pulse waves), which have been corrected by the peak corrector 328. In addition, the pulse rate measuring unit 330 also calculates the pulse interval, a pulse interval change rate, and the like.

It is noted that the pieces of acquired measurement data such as the pulse rate, the pulse interval, and the pulse interval change rate are transmitted to, for example, a PC, a portable music player having a display, a smart phone, or the like with the wireless communication module 60 interposed therebetween. In this case, in addition to the measurement results and the detection results, pieces of data such as measurement date and time are preferably transmitted.

Next, a method of using the grip-type pulse wave measuring device 1 will be described. When the grip-type pulse wave measuring device 1 is used to detect the photoplethysmographic signal and measure the pulse rate and the like, as illustrated in FIGS. 3 and 4, the user grips the grip-type pulse wave measuring device 1 by the thumb and the other four fingers of the right hand (or the left hand). In this case, as described above, when the lock is released and the user does not grip the main body portion 10, the light shielding cover 13 is automatically opened, so that the user can naturally grip the grip-type pulse wave measuring device 1.

When the user grips the main body portion 10, the user moves his/her thumb until the thumb abuts against the stopper portion 11 (from right to left in the example illustrated in FIGS. 3 and 4), whereby the light shielding cover 13 swings and is closed so as to cover the finger tip of the thumb while the end portion (end side) of the light shielding cover 13 is pushed by the thumb. Then, the finger tip of the thumb is made to make contact with the photoplethysmographic sensor 20 by placing the inner portion of the thumb on the recess 17.

With this process, the photoplethysmographic signal is acquired from the finger tip of the thumb by the photoplethysmographic sensor 20. Then, the pulse rate and the like are measured by the signal processor 31. The method of measuring the pulse rate and the like is as described above, and detailed description thereof will therefore be omitted here.

In this manner, the user can detect and measure the photoplethysmographic signal, the pulse rate, and the like only by gripping the grip-type pulse wave measuring device 1. It is note that information, such as the photoplethysmographic signal and the pulse rate that have been detected and measured, can be transmitted to the external device by the wireless communication module 60.

As described in detail above, according to the embodiment, when the user grips the device 1 (the main body portion 10) by one hand and moves his/her thumb as the measurement site onto the photoplethysmographic sensor 20, the thumb can be easily positioned on the photoplethysmographic sensor 20 by the stopper portion 11. In this case, since the light shielding cover 13 swings and is closed by being pressed by the thumb, the light shielding cover 13 covers the thumb to prevent disturbance light from entering the sensor, so that stable measurement can be performed. As a result, the pulse waves can be stably acquired with no influence by the disturbance light only by naturally gripping the device 1 by one hand without any limit of the place of use.

Further, according to the present embodiment, since the above-described light shielding cover 13 includes the biasing member 15 which biases the light shielding cover 13 in the direction of opening it, the light shielding cover 13 can be automatically opened when the device 1 (the main body portion 10) is not gripped. Therefore, the light shielding cover 13 does not become obstructive in gripping of the device 1. Thus, the user can naturally grip the device 1 (main body portion 10) without being forced to perform an unnatural movement when gripping the device 1 (main body portion 10).

According to the embodiment, the light shielding cover 13 is mounted so as to be swingable about, as the swing shaft 14, the shaft which is provided substantially in parallel to the axial direction of the main body portion 10. Therefore, with a series of natural movements of gripping the device 1 (main body portion 10) and causing the thumb to slide laterally and move onto the photoplethysmographic sensor 20, the light shielding cover 13 can be made to swing and be closed so as to cover the finger tip of the thumb.

According to the embodiment, the step portion 12 is formed in the main body portion 10 at a position closer to the tip portion at the back surface side when seen from the stopper portion 11 side. Therefore, when the user grips the device 1 (i.e., the main body 10) while making the index finger along the step portion 12, the index finger is guided to the appropriate gripping position by the step portion 12. As a result, when the user grips the device 1 (main body portion 10), the positions of the respective fingers are fixed substantially constant, and variations in the position of the finger tip of the thumb in the vertical direction (i.e., variations in the position thereof relative to the photoplethysmographic sensor 20) can be suppressed.

According to the embodiment, the area of the main body portion 10 in which the photoplethysmographic sensor 20 is disposed is recessed inward from the peripheral surface. The user can therefore reliably locate the finger tip of the thumb on the photoplethysmographic sensor 20 without viewing by putting the inner portion of the thumb on the recess 17.

According to the embodiment, the lock mechanism 16 which locks (fixes) the light shielding cover 13 in the closed state is provided. Therefore, the light shielding cover 13 can be fixed in the closed state while the device 1 is not used, so that it is possible to reduce the possibility of breakage, for example, even when it is carried, dropped, and so on.

In the above-described embodiment, the light shielding cover 13 is configured so as to be swingable (openable and closable). Alternatively, the configuration in which the light shielding cover 13 is fixed, that is, no opening/closing mechanism of the light shielding cover 13 (the swinging shaft 14, the biasing member 15, the locking mechanism 16, and the like) is provided may be employed.

Figure 7:
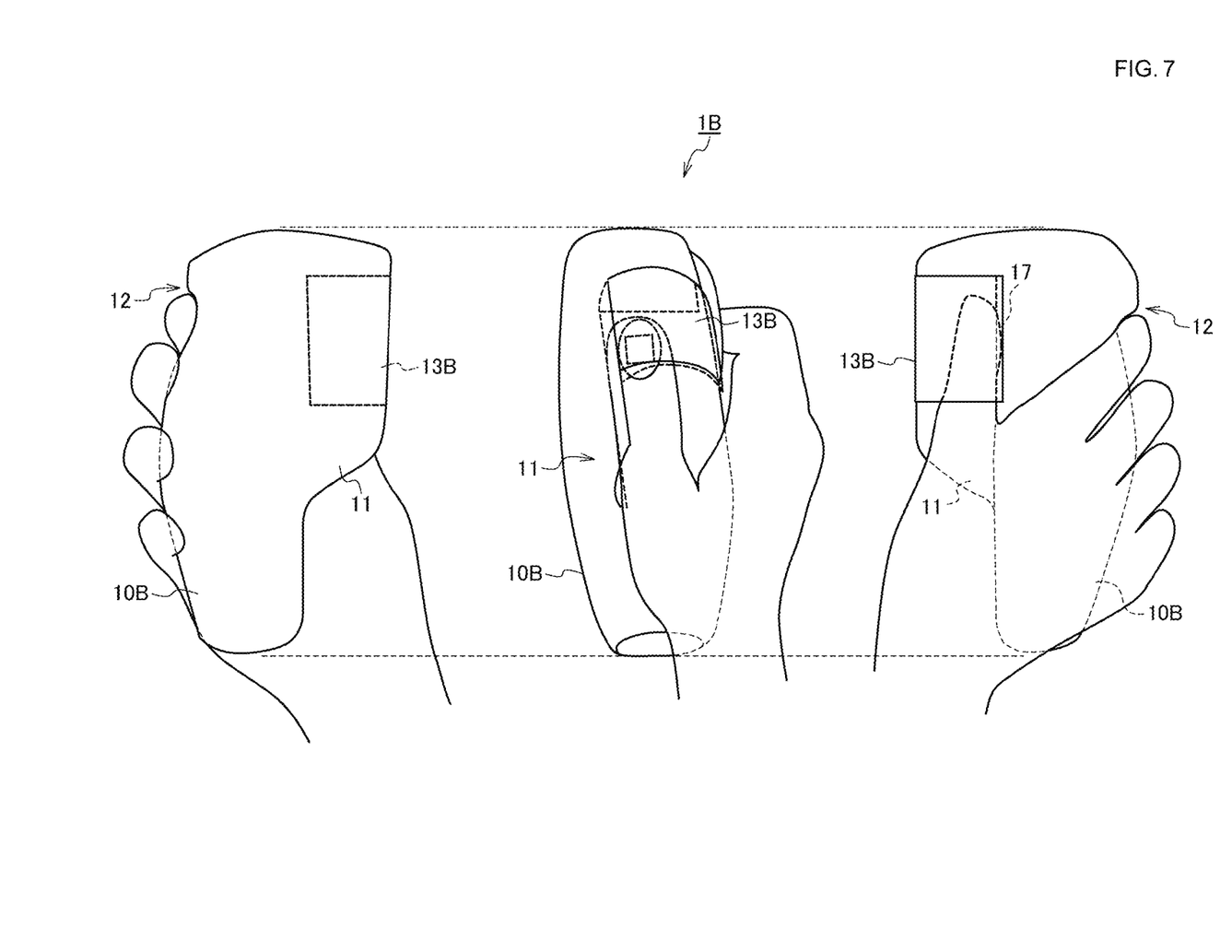
FIG. 7 is a view (front view and side views) illustrating an appearance of a grip-type pulse wave measuring device according to a modification and a state (a state in measurement) in which the grip-type pulse wave measuring device is gripped by the hand.

Next, a grip-type pulse wave measuring device 1B according to a modification will be described with reference to FIG. 7. In this case, description of the same or similar components as or to those in the above-described embodiment will be simplified or omitted, and different points will be mainly described. Specifically, FIG. 7 is a view (front view and side views) illustrating an appearance of the grip-type pulse wave measuring device 1B according to the modification and a state (a state in measurement) in which the grip-type pulse wave measuring device 1B is gripped by the hand. In FIG. 7, components that are the same as or similar to those in the above-described embodiment are denoted by the same reference numerals.

The grip-type pulse wave measuring device 1B is different from the above-described grip-type pulse wave measuring device 1 in that a light shielding cover 13B is fixed in a closed state (that is, no opening/closing mechanism (the swing shaft 14, the biasing member 15, the lock mechanism 16, and the like) is provided). It is noted that the light shielding cover 13B is formed into a substantially semi-cylindrical shape and is disposed so as to cover an upper portion of the photoplethysmographic sensor 20. The other configurations are the same as those of the above-described grip-type pulse wave measuring device 1, and detailed description thereof will therefore be omitted here.

According to this modification, similarly to the above-described embodiment, when the user grips the device 1B (main body portion 10B) by one hand, the thumb and the index finger can be guided to appropriate gripping positions by the stopper portion 11 and the step portion 12. Therefore, when the user grips the device 1B (main body portion 10B), the positions of the respective fingers are fixed substantially constant, and variations in the position of the finger tip of the thumb (i.e., variations in the position thereof relative to the photoplethysmographic sensor 20) can be suppressed. As a result, the pulse waves can be stably acquired only by naturally gripping the device 1B by one hand without any limit of the place of use. Since the step portion 12 catches the index finger, the user is not required to firmly grip the main body portion 10B and hardly feels fatigue even if he/she grips the device 1B (main body portion 10B) for a relatively long time.

According to this modification, since the light shielding cover 13B covers the photoplethysmographic sensor 20 to prevent disturbance light from entering the sensor, it is possible to stably acquire (measure) the photoplethysmographic signal.

According to this modification, the area of the main body portion 10B in which the photoplethysmographic sensor 20 is disposed is recessed inward from the peripheral surface. Therefore, the user can therefore reliably locate the finger tip of the thumb on the photoplethysmographic sensor 20 without viewing by putting the inner portion of the finger tip of the thumb on the recess 17. In particular, even when it is difficult to visually check the photoplethysmographic sensor 20 due to the light shielding cover 13B, a position (the position of the photoplethysmographic sensor 20) where the finger tip of the thumb is placed can be recognized by sense of touch. Therefore, positional variations in the finger tip of the thumb in the lateral direction and the vertical direction can be suppressed, and stable pulse wave measurement can be performed. Further, when the thumb is held for a long time in a stretched state of the first joint, the user feels fatigue in the thumb. The photoplethysmographic sensor 20 is however located in the area recessed inward from the peripheral surface, so that the thumb is bent moderately and the user hardly feels fatigue in the thumb.

Further, according to this modification, since the light shielding cover 13B has no movable portion (opening/closing mechanism), it is possible to reduce the weight and cost of the grip-type pulse wave measuring device 1B and to improve durability.

While the embodiment of the invention has been described above, it should be appreciated the invention is not limited to the above embodiment, and various modifications can be made. For example, in the above embodiment, the case in which the device 1 is gripped by the right hand has been described as the example. Alternatively, the shape of the grip-type pulse wave measuring device 1 may be made different in such a manner that the stopper portion 11 is provided at a symmetrically opposite position between right-hand use when the device is gripped by the right hand and left-hand use when the device is gripped by the left hand.

Although the stopper portion 11 is formed so as to abut against the left side surface of the thumb in the above embodiment, the stopper portion 11 may be formed so as to abut against a right side surface of the thumb (in a symmetrically opposite manner to that in the above embodiment).

Further, in the above embodiment, the grip-type pulse wave measuring device 1 includes the photoplethysmographic sensor 20. Alternatively, for example, a piezoelectric pulse wave sensor or an oxygen saturation sensor may be used instead of the photoplethysmographic sensor 20.

In the above embodiment, pieces of information (measurement data) such as the photoplethysmographic signal and the pulse rate, which have been detected and measured, are transmitted to the external device by the wireless communication module 60. Alternatively, the pieces of acquired information (measurement data) may be stored in a memory in the device during measurement, and the device may be connected to the external device and the pieces of information may be transferred thereto after the measurement is finished.

REFERENCE SIGNS LIST 1, 1B GRIP-TYPE PULSE WAVE MEASURING DEVICE
10, 10B MAIN BODY PORTION
11 STOPPER PORTION
12 STEP PORTION
13, 13B LIGHT SHIELDING COVER
14 SWING SHAFT
15 BIASING MEMBER
16 LOCK MECHANISM
17 RECESS
20 PHOTOPLETHYSMOGRAPHIC SENSOR
201 LIGHT EMITTING ELEMENT
201 LIGHT RECEIVING ELEMENT
60 WIRELESS COMMUNICATION MODULE

The invention claimed is:

1. A grip-type pulse wave measuring device comprising:
a main body having a contoured shape configured to be gripped by a hand of a user, the main body having a spheroid shape;
a stopper that projects from a side of the main body that extends in a longest direction of the main body and is configured to abut against a side surface of a thumb of the hand of the user, such that the stopper is configured to restrict a position of the thumb when the hand of the user grips the main body;
a pulse wave sensor disposed at a position offset from the stopper in a peripheral direction of the main body, with the pulse wave sensor configured to acquire a pulse wave signal from a finger tip of the thumb, the pulse wave sensor including a light emitting element and a light receiving element, wherein the light emitting element and the light receiving element are both completely covered by a single uniformly flat transparent cover and separated by a region comprising a resin and having a light shielding property; and
a step disposed on the main body at a position closer to an end of the main body at a back surface side relative to the side of the main body from which the stopper projects,
wherein the step is configured to position the hand when the user grips the main body by directing an index finger of the hand, such that the finger tip of the thumb is physically guided to the pulse wave sensor.

2. The grip-type pulse wave measuring device according to claim 1, wherein the pulse wave sensor is disposed in an inwardly recessed area in the main body relative to a peripheral surface of the main body;
wherein, in the direction from stopper toward the step, the stopper and the step are arranged so as to sandwich the main body, and
wherein the step includes a depression.

3. The grip-type pulse wave measuring device according to claim 1, further comprising a light shielding cover having a substantially semi-cylindrical shape and disposed to cover an upper portion of the pulse wave sensor relative to the thumb of the user.

4. The grip-type pulse wave measuring device according to claim 3, wherein the pulse wave sensor is a photoplethysmographic sensor having a light emitting element and a light receiving element configured to acquire a photoplethysmographic signal;
wherein the light emitting element and the light receiving element are covered by a transparent cover and separated by a region comprising a resin and having a light shielding property.

5. The grip-type pulse wave measuring device according to claim 4, wherein the photoplethysmographic sensor is configured to obtain the photoplethysmographic signal from the finger tip of the thumb.

6. The grip-type pulse wave measuring device according to claim 4, wherein the light shielding cover is mounted to the main body and configured to swing in the peripheral direction of the main body.

7. The grip-type pulse wave measuring device according to claim 6, wherein the light shielding cover includes a biasing member configured to bias the light shielding cover in a direction to open the light shielding cover and is mounted to the main body to be swingable, such that when seen from a base of the main body, one end of the light shielding cover protrudes towards a side of the pulse wave sensor relative to the stopper in an open state, and another end of the light shielding cover is flush with the stopper in a closed state.

8. The grip-type pulse wave measuring device according to claim 6, wherein the light shielding cover is swingable about a shaft extending parallel to the longest direction of the main body.

9. The grip-type pulse wave measuring device according to claim 7, further comprising a lock mechanism configured to lock the light shielding cover in a closed state.

10. A grip-type pulse wave measuring device comprising:
a main body having a spheroid shape configured to position a hand in a defined orientation when gripped by a user;
a stopper projecting from a front surface of the spheroid shaped main body that extends in a longest direction thereof, such that stopper is configured to position a thumb of the user in a defined position when the user grips the spheroid shaped main body;
a pulse wave sensor disposed at a position offset from the stopper in a peripheral direction of the spheroid shaped main body, with the pulse wave sensor configured to acquire a pulse wave signal from the user, the pulse wave sensor including a light emitting element and a light receiving element, wherein the light emitting element and the light receiving element are both completely covered by a single uniformly flat transparent cover and separated by a region comprising a resin and having a light shielding property; and
a step disposed on a back surface of the spheroid shaped main body opposite the front surface, with the step being configured to direct an index finger of the hand when the user grips the main body, such that the thumb is physically guided to the pulse wave sensor.

11. The grip-type pulse wave measuring device according to claim 10,
wherein the pulse wave sensor is disposed in an inwardly recessed area in the main body relative to a peripheral surface of the main body,
wherein, in the direction from stopper toward the step, the stopper and the step are arranged so as to sandwich the main body, and
wherein the step includes a depression.

12. The grip-type pulse wave measuring device according to claim 10, further comprising a light shielding cover having a substantially semi-cylindrical shape and disposed to cover an upper portion of the pulse wave sensor relative to the thumb of the user.

13. The grip-type pulse wave measuring device according to claim 12,
wherein the pulse wave sensor is a photoplethysmographic sensor having a light emitting element and a light receiving element configured to acquire a photoplethysmographic signal,
wherein the light emitting element and the light receiving element are covered by a transparent cover and separated by a region comprising a resin and having a light shielding property.

14. The grip-type pulse wave measuring device according to claim 13, wherein the photoplethysmographic sensor is configured to obtain the photoplethysmographic signal from a finger tip of the thumb.

15. The grip-type pulse wave measuring device according to claim 13, wherein the light shielding cover is mounted to the main body and configured to swing in the peripheral direction of the main body.

16. The grip-type pulse wave measuring device according to claim 15, wherein the light shielding cover includes a biasing member configured to bias the light shielding cover in a direction to open the light shielding cover and is mounted to the main body to be swingable, such that when seen from a base of the main body, one end of the light shielding cover protrudes towards a side of the pulse wave sensor relative to the stopper in an open state, and another end of the light shielding cover is flush with the stopper in a closed state.

17. The grip-type pulse wave measuring device according to claim 15, wherein the light shielding cover is swingable about a shaft extending parallel to the longest direction of the main body.

18. The grip-type pulse wave measuring device according to claim 16, further comprising a lock mechanism configured to lock the light shielding cover in a closed state.

* * * * *